United States Patent [19] [11] Patent Number: 6,153,385
Debatin et al. [45] Date of Patent: Nov. 28, 2000

[54] PROCESS FOR DETECTING THE EXPRESSION OF CD95 LIGAND IN CELLS

[75] Inventors: Klaus-Michael Debatin, Ulm; Ingrid Herr, Bretten, both of Germany

[73] Assignee: Deutsches Krebsforschungszentrum Stiftung des Offentlichen Rechts, Heidelberg, Germany

[21] Appl. No.: 09/077,690

[22] PCT Filed: Nov. 27, 1996

[86] PCT No.: PCT/DE96/02274

§ 371 Date: Oct. 21, 1998

§ 102(e) Date: Oct. 21, 1998

[87] PCT Pub. No.: WO97/20067

PCT Pub. Date: Jun. 5, 1997

[30] Foreign Application Priority Data

Nov. 28, 1995 [DE] Germany ............... 195 44 332

[51] Int. Cl.[7] .............. C12Q 1/68; C12P 19/34; C07H 21/04

[52] U.S. Cl. ............ 435/6; 435/91.2; 435/91.51; 536/24.31; 536/24.33

[58] Field of Search ............ 435/6, 91.2, 91.51; 536/24.31, 24.33

[56] References Cited

FOREIGN PATENT DOCUMENTS 0 675 200  10/1995  European Pat. Off. .
WO 91 02817  3/1991  WIPO .

OTHER PUBLICATIONS

Suda, T. et al. Cell 75:1169–1178, Dec. 1993.
Chomczynski and Sacchi, 1987, *Anal. Biochem.* 162:156–159.
Debatin et al., 1995, "Involvement of the APO–1 (FAS–CD95) system in T cell depletion in AIDS," *Blood* 86(10 Suppl. 1):288A; 37th Annual Meeting of the American Society of Hematology, Seattle, Washington, USA Dec. 1–5, 1995.
Dhein et al., 1995, "Autocrine T–cell suicide by APO–1," *Nature* 373:438–441.
Herr et al., 1995, "Development of a quantitative RT–PCR for the human APO–1 (FAS–CD95) ligand and monitoring of ligand expression in normal and malignant Tcells," *Blood* 86 (10 Suppl. 1):163A; 37th Annual Meeting of the American Society of Hematology, Seattle, Washington, USA, Dec. 1–5, 1995.
Herr et al., 1993, "Monitoring of CD95 ligand expression in human T cells by quantitative RT–PCR," *Cell Death and Differentiation* 3:299–305.
Panayiotidis et al., 1995, "Expression and function of the FAS antigen in B chronic lymphocytic leukemia and hairy cell leukemia," *Leukemia* 9:1227–1232.
Takahashi et al., 1994, "Human FAS ligand: gene structure, chromosomal location and species specificity," *Int. Immunol* 6:1567–1574.

*Primary Examiner*—Carla J. Myers
*Assistant Examiner*—Diana Johannsen
*Attorney, Agent, or Firm*—Pennie & Edmonds LLP

[57] ABSTRACT

The present invention relates to a process for quantitatively determining CD95 ligand, comprising the following processing steps:
  (a) isolation of total RNA from cells,
  (b) transcription the total RNA from (a) into cDNA by reverse transcription, and
  (c) amplification of the cDNA from (b) and a CD95 ligand competitor fragment by CD95 ligand-specific primers in a PCR reaction.

The process is suitable for determining the extent and/or course of apoptosis.

5 Claims, 3 Drawing Sheets

PROCESS FOR DETECTING THE EXPRESSION OF CD95 LIGAND IN CELLS

This is a national phase filing of the Application No. PCT/DE96/02274, which was filed with the Patent Corporation Treaty on Nov. 27, 1996, and is entitled to priority of the German Patent Application P 195 44 332.2, filed Nov. 28, 1995.

FIELD OF THE INVENTION

The present invention relates to a process for detecting the expression of CD95 ligand in cells.

BACKGROUND OF THE INVENTION

Apoptosis is the designation for programmed cell death. It is found e.g. in organogenesis and metamorphosis, tissue atrophy and tumor regression. Apoptosis is linked with a condensation of the cytoplasm, a loss of plasma membrane villi, a segmentation of the nucleus and extensive degradation of chromosomal DNA. It has turned out that disturbances of apoptosis occur in various diseases such as AIDS, autoimmune diseases, tumors and leukemias. In the case of AIDS, increased apoptosis seems to be responsible for the strong decrease of the CD4-T cells.

In activated T cells and in other cells there is found a cell surface protein referred to as CD95 and APO-1, respectively. A soluble or membrane-bound protein referred to as CD95 ligand and APO-1 ligand, respectively, can bind to this cell surface protein and trigger the induction of apoptosis.

The extent and course of apoptosis as well as the molecules causing the same cannot be determined so far. However, this would be necessary to be able to carry out e.g. follow-ups and suitable therapeutic measures in patients suffering from the above-mentioned diseases.

Therefore, it is the object of the present invention to provide a product serving for determining the extent of apoptosis and its course, respectively.

SUMMARY OF THE INVENTION

The present invention relates to a process for quantitatively determining CD95 ligand, comprising the following processing steps:

(a) isolation of total RNA from cells, (b) transcription the total RNA from (a) into cDNA by reverse transcription, and (c) amplification of the cDNA from (b) and a CD95 ligand competitor fragment by CD95 ligand-specific primers in a PCR reaction.

The process is suitable for determining the extent and/or course of apoptosis.

(A) The wild-type fragment and its specific primers for PCR amplification, $L_{up}$ and $L_{down}$, are shown.

(B) $L_{up}$ and $L_{upOV}$ are used for the $1^{st}$ PCR. $L_{upOV}$ binds in the middle of the sequence and contains an overhanging sequence at the 5' end having a length of 50 bp.

(C) $L_{down}$ and $L_{downOV}$ are used for the second PCR. The last 30 bp at the 5' end of $L_{downOV}$ are overhanging and complementary to the last 30 bp at the 5' end of $L_{upOV}$. The complementary regions are shown in brush-shaped fashion.

(D) shows the PCR products from the first and second PCRs, 349 and 230 bp long DNA pieces. Following purification, both fragments are hybridized with each other via their complementary regions.

(E) The fragments hybridized in (D) are used as a matrix for a third PCR reaction where $L_{up}$ and $L_{down}$ are used again as primers.

(F) The result is a mutated fragment of CD95-L which carries a 50 bp long insert in the middle of the sequence.

Figure 3:
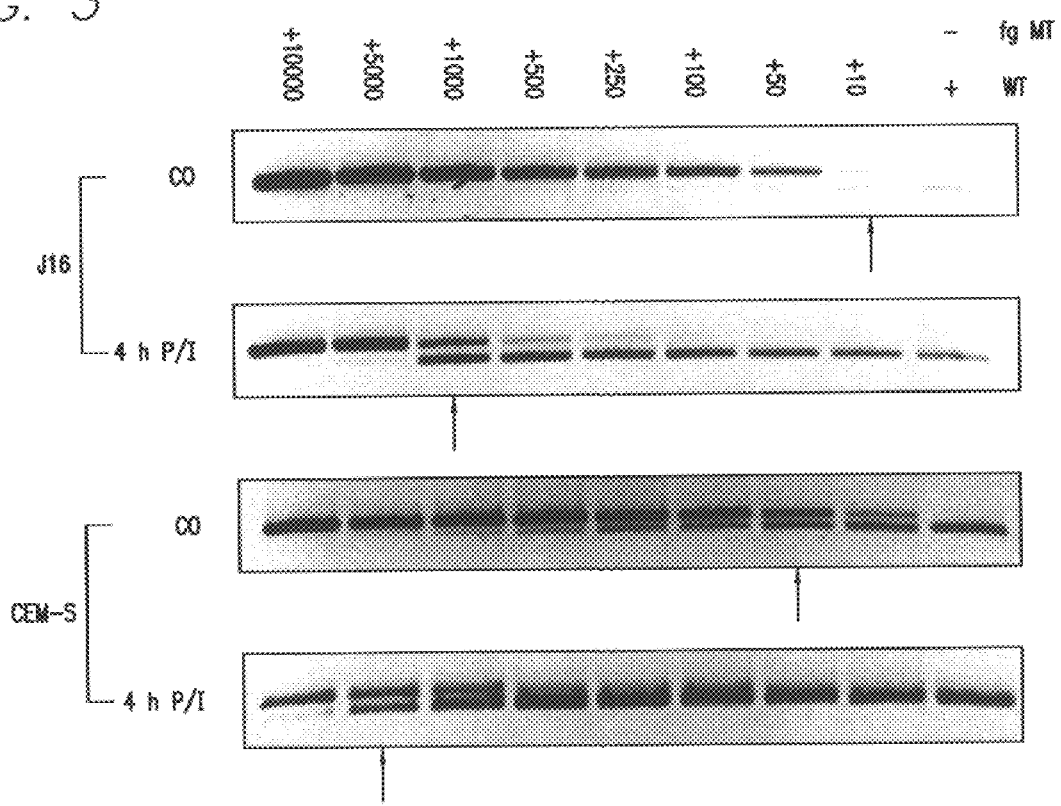

FIG. 3 shows a constitutive and induced expression of CD95-L mRNA in lymphoid cells.

DETAILED DESCRIPTION OF THE INVENTION

It is the object of the present invention to provide a product serving for determining the extent of apoptosis and its course. According to the invention this is achieved by the subject matters defined in the claims.

Therefore, the subject matter of the present invention relates to a process by which the CD95 ligand, hereinafter referred to as CD95-L, can be determined quantitatively in cells.

The present invention is based on the applicant's finding that apoptosis is caused in T cells by an increased amount of CD95-L. Furthermore, the applicant discovered that the apoptosis rate is determined by the CD95-L amount.

Figure 1:
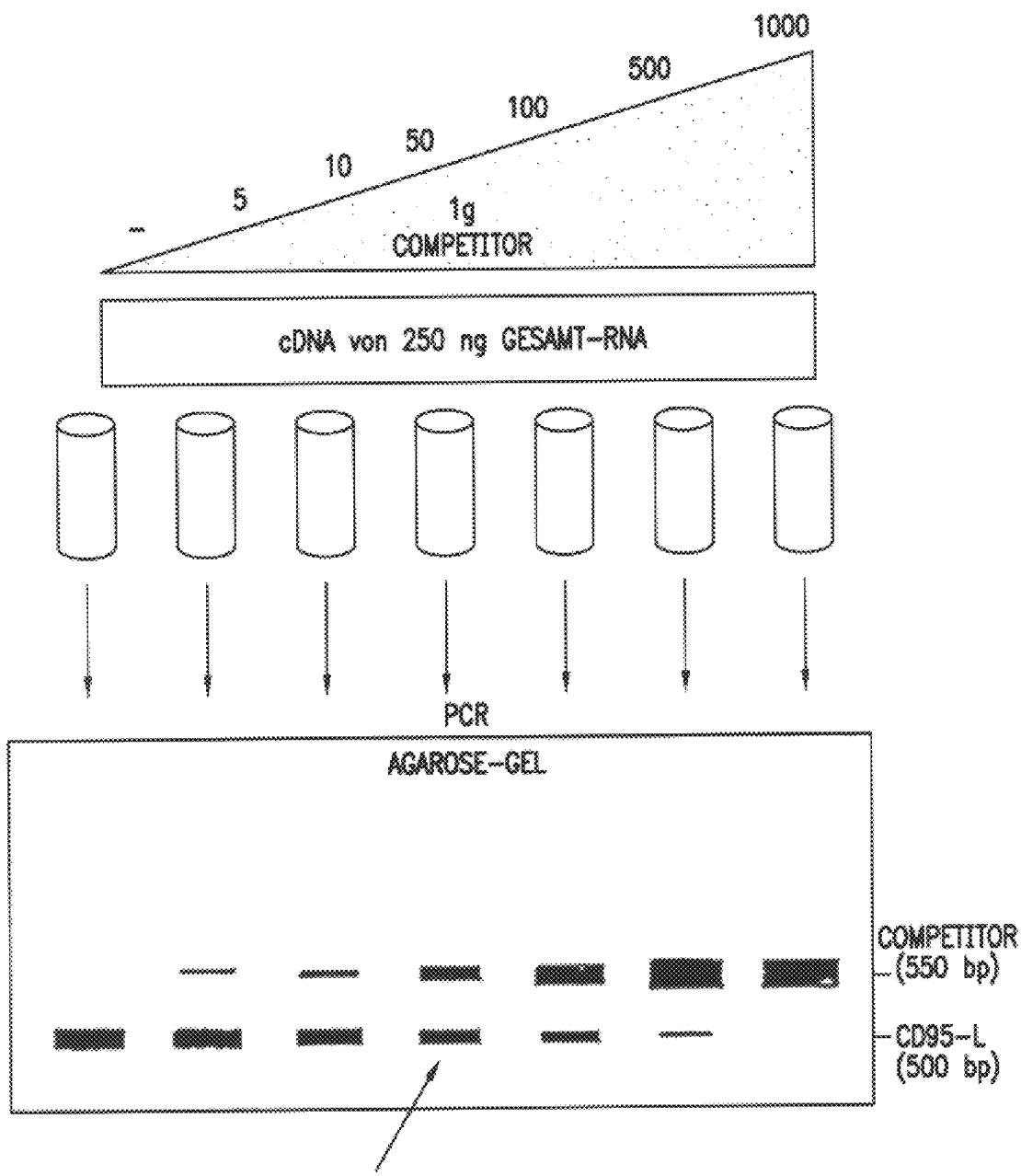
FIG. 1 shows a diagram of the quantitative PCR according to the invention for CD95-L.

The process according to the invention relates to a quantitative "polymerase chain reaction" (PCR) by which the amount of CD95-L in cells can be determined reliably. The amount of CD95-L mRNA present in the cell is determined in the process according to the invention by an RT-PCR reaction. In the quantitative PCR for CD95-L, the amount of CD95-L cDNA is titrated by adding a CD95-L-specific DNA competitor fragment to the PCR reaction. The complete reverse transcription of a defined amount of total RNA into cDNA precedes this step. The competitor fragment differs from the "wild-type" cDNA of CD95-L by additional base pairs in the middle of the nucleotide sequence but has identical flanking sequences. Therefore, wild-type and competitor fragment are recognized by the same primer combination and can be multiplied jointly in a PCR. Due to the identical primer binding sites and the similar nucleotide sequences, both fragments are subject to the same amplification rate. However, the minor difference in size permits the separation of both DNA species by gel electrophoresis according to PCR. The intensities of the DNA bands on agarose gel reflect the original amounts of cDNA used in PCR. If the results of CD95-L and competitor DNA bands on the gel are identical, it can be concluded that the same initial concentrations of competitor and CD95-L were present. The amount of CD95-L cDNA titrated in this way reflects the amount of CD95-L mRNA in the total RNA, since the reverse transcription proceeds fully. The diagram of the quantitative PCR reaction is shown in FIG. 1.

The quantitative PCR is based on the following reaction principle. For quantifying the CD95-L expression rate, cDNA of a certain amount of reversely transcribed total RNA is pipetted into PCR vessels. Competitor fragment in various dilutions, e.g. from 5 to 10000 fg, is added to each sample with the exception of the negative control (−). Following the PCR reaction, the amplified DNA fragments are treated with ethidium bromide and separated on an agarose gel. The DNA is made visible by irradiating the gel with U.V. light. The titration point (in FIG. 1 marked by an arrow) is determined, with respect to which both the bands of the CD95-L DNA and the bands of the competitor DNA have equal intensities. An equal ratio of both bands shows that equal amounts of DNA to be determined and competitor DNA have been amplified. Correspondingly, the amount of CD95-L cDNA determined by the titration point (to be equated with the amount of mRNA) had been present in the employed amount of total RNA.

The primers synthesized for PCR are based preferably on the published sequence of CD95-L (cf. Takahashi T. et al., Int. Immunol. 6, (1984), 1547–1567). PCR is carried out under conditions with which a person skilled in the art is familiar.

For example, the following primers can be used for amplifying the CD95-L fragment (about 500 bp) and the competitor fragment (about 550 bp)

$L_{up}$ 5'-ATGTTTCAGCTCTTCCACCTACAGA-3' (SEQ ID NO: 1)(25 mer, binds to nucleotides 301 to 325 of the CD95-L sequence)

$L_{down}$ 5'-CCAGAGAGAGCTCAGATACGTTGAC-3' (SEQ ID NO: 2) (25 mer, binds to nucleotides 775 to 799 of the CD95-L sequence)

Furthermore, e.g. the following primers can be used for the preparation of the competitor fragment (550 bp)

$L_{upOV}$
5'-GGATCCGTACTACAGTGAAATTATGGAAGG-GTATCCGAGTTCAGG-AATTCCAGAGGCATGGACCTTGAGTTGGACT-TGCC-3' (SEQ ID NO: 3) (80 mer, binds to nucleotides 451 to 480)

$L_{downOV}$
5'-CCTTCCATAATTTCACTGTAGTACGGATCCG-AATGGGAAGACACCTATGGAATTGTCC-3' (SEQ ID NO: 4) (58 mer, binds to nucleotides 481 to 508)

Figure 2:
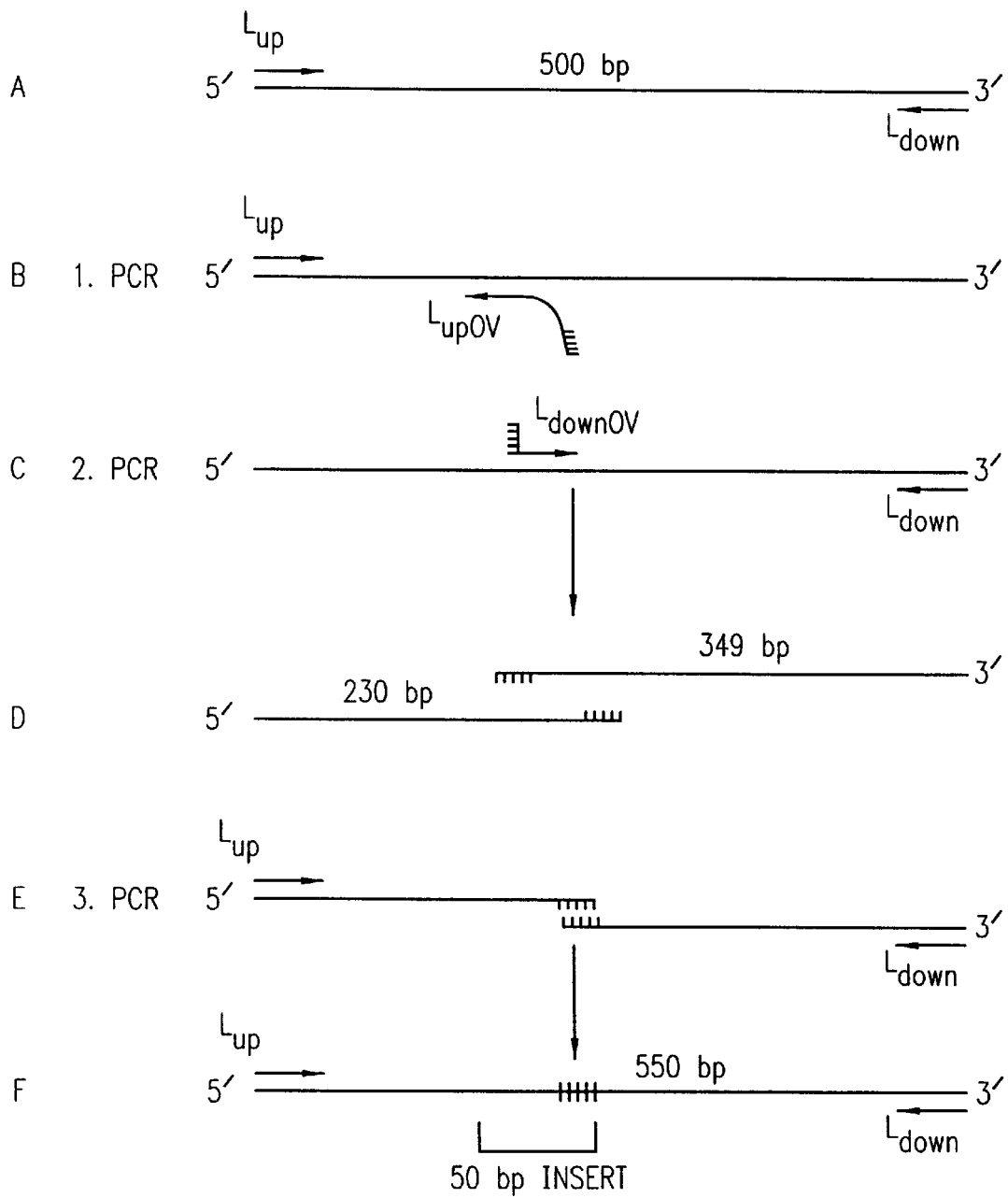
FIG. 2 shows a diagram for the preparation of a competitor DNA fragment of CD95-L.

The mutated CD95-L fragment which is used in PCR as competitor fragment, is prepared by mutagenesis, preferably PCR mutagenesis. CD95-L CDNA originating e.g. from T cell line CEM-S serves as a matrix for PCR mutagenesis. Two parts of the $L_{up}/L_{down}$ PCR fragment are amplified by using in a PCR the primer pair $L_{up}/L_{upOV}$ (yields a fragment having a length of 230 bp) and in a second PCR the primer pair $L_{down}/L_{downOV}$ (yields a fragment which has a length of 349 bp). The primer $L_{upOV}$ contains a 50 bp long overhanging sequence which is complementary to a 30 bp long overhanging sequence of the primer $L_{downOV}$. Following purification, the two fragments are hybridized via their complementary regions and used as a matrix for another PCR amplification with primers $L_{up}/L_{down}$. The result is a mutated fragment of CD95-L which contains 50 additional bases in the middle of the nucleotide sequence. The diagram for the preparation of the competitor fragment is illustrated in FIG. 2.

The process according to the invention, which is based on a competition between a mutant fragment and a wild-type fragment, enables an accurate determination of the intracellular level of CD95-L in small amounts of sample (1 to 5×106 cells).

Since the apoptosis conveyed by CD95/CD95-L obviously takes part in T cell depletion in the case of an AIDS disease, the quantitative determination of the expression of CD95-L can be used for the follow-up and as an indicator of therapeutic interventions in AIDS patients. Furthermore, the process according to the invention is suitable in vitro for "drug screening" for potential drugs which can block virus-induced, CD95-conveyed apoptosis in T cells. Likewise, the quantitative determination of the CD95 ligands in cells can be used for the disease definition, follow-up and the pharmacological influence of ligand expression in "drug screening" in the case of diseases accompanied by reduced apoptosis (e.g. leukemias) or increased CD95-conveyed apoptosis. A direct field of application is represented e.g. by the analysis of the effect of drugs, such as azothioprin, cyclosporin A, cyclophosphamide, cortisone and methotrexate, which are presently used for the immunosuppressive treatment of autoimmune diseases and transplant rejections.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLES

A. Example 1

Determination of CD95-L in Lymphoid Cells

The lymphoid T cells J16 and CEM-S were cultivated in common broth each and treated with PMA (5 ng/ml) as well as ionomycin (2 µg/ml), respectively, for 4 hours and 24 hours, respectively. Total RNA was obtained from the cells according to the method by Chomczynski, P. and Sacchi, N., Anal. Biochem., 162, (1987), 156–159 and transcribed by means of AMV reverse transcriptase (Amersham, Braunschweig, FRG) and oligo-dT16 primers (Promega, Heidelberg, FRG) into cDNA. A 20 µl reaction comprised 1× AMV buffer (50 mM TrisHCl, pH 8.3; 8 mM $MgCl_2$; 50 mM NaCl; 1 mM DTT), 250 µM of each dNTP (Pharmacia, Freiburg, FRG), 0.5 µM oligo-$dT_{16}$; 0.6 (U/µl RNase inhibitor (Amersham, Braunschweig, FRG); 0.75 U/µl AMV reverse transcriptase; 50 ng/µl total RNA (prior to the addition denatured at 65° C. for 5 minutes). Reverse transcription was carried out at 42° C. for 45 minutes, and the reaction was then terminated by heating to 94° C. for 5 minutes. Since all reagents were present in excess, it can be assumed that the RNA employed has been transcribed completely into cDNA.

For quantifying the CD95-L expression rate, cDNA of 250 ng of reversely transcribed total RNA each was pipetted into PCR vessels. Competitor fragment, as described above, was added in differing dilutions of 10 to 10000 fg to each sample with the exception of the negative control (−). The reaction mixture comprised: 50 µl, containing cDNA (=250 ng of reversely transcribed total RNA), 1× PCR buffer (10 mM Tris-HCl, pH 8.8; 50 mM KCl, 0.08% NP40), 1 mM $MgCl_2$, 200 µM dNTPs, 0.5 µM primers and 1.12 U/vessel Taq polymerase (MBI/Fermentas). The amplification was carried out in a robocycler (Stratagene) or a Biozym thermocycler using the $L_{up}$ and $L_{down}$ primers as described above. The reaction conditions were as follows: 35 seconds at 94° C., 90 seconds at 56° C. and 120 seconds at 72° C. over 36 cycles. 20 µl of the PCR reaction were separated by electrophoresis on a 2% agarose gel and, following ethidium bromide staining, were made visible by U.V. light. The point at which both the bands of the CD95-L DNA and the bands of the competitor DNA had equal intensities was determined on the gel. The gel is shown in FIG. 3. Equal band intensities which indicate identical amounts of wild-type and competitor fragment, are marked by arrows.

It showed that untreated J16 cells expressed 10 fg CD95-L mRNA/250 ng total RNA and untreated CEM-S cells expressed 50 fg CD95-L mRNA/250 ng total RNA. A PMA/ionomycin treatment increased the expression of CD95-L mRNA to 1000 fg/250 ng of total RNA in the case of J16 cells and to 5000 fg/250 ng of total RNA in the case of CEM-S cells (cf. Table 1).

The above data show that CD95-L can be determined quantitatively by the process according to the invention. Thus, the extent and/or the course of apoptosis, particularly in the case of diseases such as AIDS, can be determined.

TABLE 1

Expression of CD95-L mRNA (fg/250 ng total RNA) in lymphoid cell lines

|  |  | CO | 4 h P/I | 24 h P/I |
| --- | --- | --- | --- | --- |
| T cell lines | J 16 | 10 | 1000 | 1000 |
|  | CEM-S | 50 | 5000 | 250 |

All references cited within the body of the instant specification are hereby incorporated by reference in their entirety.

What is claimed:

1. A process for quantifying a CD95 ligand, comprising:

(a) isolating RNA from cells;

(b) transcribing said RNA of step (a) into cDNA by reverse transcription;

(c) amplifying said cDNA of step (b) and a defined amount of CD95 ligand competitor fragment using CD95 ligand-specific primers, wherein the CD95 ligand-specific primers have the following sequences:

$L_{up}$ 5'-ATGTTTCAGCTCTTCCACCTACAGA-3' (SEQ ID NO: 1) and $L_{down}$ 5'-CCAGAGAGAGCTCAGATACGTTGAC-3' (SEQ ID NO: 2), so that a CD95 ligand amplification product of the cDNA of step (b) and a CD95 ligand competitor amplification product are generated; and (d) quantifying said CD95 ligand by comparing the quantity of CD95 ligand amplification product with the quantity of CD95 ligand competitor amplification product.

2. The process of claim 1, wherein the cells originate from an established cell line or a patient.

3. The process of claim 2, wherein the cells are lymphoid T cells.

4. A method for detecting apoptosis, comprising:

(a) isolating RNA from T cells;

(b) transcribing said RNA of step (a) into cDNA by reverse transcription;

(c) amplifying said cDNA of step (b) and a defined amount of CD95 ligand competitor fragment using CD95 ligand-specific primers, wherein the CD95 ligand specific primers have the following sequences:

$L_{up}$ 5'-ATGTTTCAGCTCTTCCACCTACAGA-3' (SEQ ID NO: 1) and $L_{down}$ 5'-CCAGAGAGAGCTCAGATACGTTGAC-3' (SEQ ID NO: 2), so that a CD95 ligand amplification product of the cDNA of step (b) and a CD95 ligand competitor amplification product are generated;

(d) quantifying said CD95 ligand by comparing the quantity of CD95 ligand amplification product with the quantity of CD95 ligand competitor amplification product, wherein an increased quantity of CD95 ligand compared to control T cells is indicative of apoptosis.

5. The method of claim 4, wherein the T cells in step (a) are from an AIDS patient.

* * * * *

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
atgtttcagc tcttccacct acaga        25

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
ccagagagag ctcagatacg ttgac        25

<210> SEQ ID NO 3
<211> LENGTH: 80
<212> TYPE: DNA
<213> ORGANISM: Artificial Sequence
<220> FEATURE:
<223> OTHER INFORMATION: Primer

<400> SEQUENCE: 3
ggatccgtac tacagtgaaa ttatggaagg gtatccgagt tcaggaattc cagaggcatg        60
gaccttgagt tggacttgcc        80

<210> SEQ ID NO 4
<211> LENGTH: 58
<212> TYPE: DNA
<213> ORGANISM: Artificial Sequence
<220> FEATURE:
<223> OTHER INFORMATION: Primer

<400> SEQUENCE: 4
ccttccataa tttcactgta gtacggatcc gaatgggaag acacctatgg aattgtcc        58